| United States Patent [19] | [11] | 4,210,643 |
|---|---|---|
| Fleisch et al. | [45] | * Jul. 1, 1980 |

[54] PHOSPHONATE PHARMACEUTICAL COMPOSITION

[75] Inventors: Herbert A. Fleisch; Rolf Felix, both of Bern, Switzerland

[73] Assignee: The Procter & Gamble Company, Cincinnati, Ohio

[*] Notice: The portion of the term of this patent subsequent to Sep. 12, 1995, has been disclaimed.

[21] Appl. No.: 915,026

[22] Filed: Jun. 12, 1978

Related U.S. Application Data

[63] Continuation of Ser. No. 792,946, May 2, 1977, Pat. No. 4,113,861.

[51] Int. Cl.² .............................................. A61K 31/66
[52] U.S. Cl. ............................................. 424/204
[58] Field of Search ........................................ 424/204

[56] References Cited

U.S. PATENT DOCUMENTS 3,442,604  5/1969  Smith et al. ........................... 424/204

FOREIGN PATENT DOCUMENTS 2013426 10/1971 Fed. Rep. of Germany ........... 424/204
463023 11/1968 Switzerland .............................. 424/204

Primary Examiner—Frederick E. Waddell
Attorney, Agent, or Firm—Jerry J. Yetter; Richard C. Witte; Julius P. Filcik

[57] ABSTRACT

Certain phosphonate materials affect carbohydrate metabolism.

1 Claim, No Drawings

PHOSPHONATE PHARMACEUTICAL COMPOSITION

This is a continuation, of application Ser. No. 792,946, filed May 2, 1977, now U.S. Pat. No. 4,113,861.

BACKGROUND OF THE INVENTION

The present invention relates to compositions and processes for affecting carbohydrate metabolism. More specifically, certain alkyl diphosphonates are administered to humans and lower animals to desirably influence carbohydrate metabolism. In particular, the compositions and processes herein are especially useful for affecting the metabolism of glucose and are useful in the treatment of diabetes.

SUMMARY OF THE INVENTION

The present invention encompasses a method for promoting the metabolism of carbohydrates, especially glucose, in humans and lower animals comprising administering to a human or lower animal in need of such treatment a safe and effective amount of a pharmaceutically-acceptable diphosphonate compound ("phosphonate") of the type described more fully hereinafter.

By the practice of this invention, disease states involving decreased metabolism of carbohydrates, especially glucose, are effectively treated. Accordingly, the present invention provides an effective means for the treatment of diabetes (*diabetes mellitus*).

SUMMARY OF THE INVENTION

The present invention encompasses a process for desirably affecting the metabolism of carbohydrates, especially glucose, comprising administering to a human or lower animal in need of such treatment a safe and effective amount of a pharmaceutically-acceptable geminal diphosphonate material of the type described more fully hereinafter.

The present invention provides a means of treating disease states involving decreased metabolism of carbohydrates, especially glucose, and thus provides a means for treating *diabetes mellitus* which comprises administering to a human suffering from *diabetes mellitus* a safe and effective amount of a pharmaceutically-acceptable phosphonate compound.

DISCUSSION OF RELATED REFERENCES

Various phosphonate compounds are reported in the literature as being useful in the treatment of anomalous mobilization and deposition of calcium phosphate salts (bone mineral) in humans and other animals. See especially the U.S. Pat. Nos. of M. D. Francis: 3,683,080, granted Aug. 8, 1972; 3,678,164, granted July 18, 1972; 3,662,066, granted May 9, 1972; 3,553,314, granted Jan. 5, 1971; 3,553,315, granted Jan. 5, 1971; 3,584,124, granted June 8, 1971; 3,584,125, granted June 8, 1971; and 3,641,246, granted Feb. 8, 1972; as well as German DT No. 2360-798 (June 26, 1975); German DT No. 2343-146 (Mar. 6, 1975); and Belgian BE No. 822-929 (Dec. 6, 1973).

In contrast with the prior art disclosures of the use of phosphonate materials to prevent the formation of anomalous, calcified mineral deposits in bones, joints and soft tissues, the present invention is based on the new discovery that certain, select phosphonates unexpectedly and importantly affect carbohydrate metabolism at the cellular level.

The copending application of Felix and Fleisch, entitled CARBOXY PHOSPHONATE PHARMACEUTICAL COMPOSITION, Ser. No. 792,947, filed May 2, 1977, discloses the use of certain vicinal and geminal carboxy phosphonates to desirably affect glucose metabolism.

DETAILED DESCRIPTION OF THE INVENTION

The treatment regimens of this invention employ a safe and effective amount of a pharmaceutically-acceptable geminal diphosphonate compound. These compounds are administered to treat diseases involving carbohydrate metabolism in humans and lower animals in need of such treatment. The geminal diphosphonates used herein are conveniently referred to as "phosphonates."

By "safe and effective amount of phosphonate compound" herein is meant sufficient phosphonate compound to desirably affect carbohydrate (especially glucose) metabolism, at a reasonable benefit/risk ratio attendant with any medical treatment. Within the scope of sound medical judgment, the dosage of phosphonate compound will vary with the particular condition being treated, the severity of the condition, the duration of the treatment, the specific phosphonate compound employed, and like considerations as disclosed more fully hereinafter.

By "pharmaceutically-acceptable" herein is meant that the phosphonate drug compound and other ingredients used in the compositions employed herein are suitable for use in contact with the tissues of humans and lower animals without undue toxicity, irritation, allergic response, and the like, commensurate with a reasonable benefit/risk ratio.

The term "administration" of the phosphonate compounds and compositions herein includes systemic use, as by injection (especially parenterally), intravenous infusion suppositories and oral administration thereof.

By the term "comprising" as used herein is meant that various other, compatible drugs and medicaments, as well as inert ingredients, can be conjointly employed in the compositions and processes of this invention, as long as the critical phosphonate compounds are used in the manner disclosed. The term "comprising" thus encompasses and includes the more restrictive terms "consisting of" and "consisting essentially of" which characterize the use of the essential phosphonate compounds in the practice of this invention.

By "compatible" herein is meant that the components of the compositions which can be used in the practice of this invention are capable of being commingled without interacting in a manner which would substantially decrease the efficacy of the phosphonate compositions under ordinary use situations.

All percentages herein are by weight, unless otherwise specified.

The phosphonate compounds used in the practice of this invention are of the formula

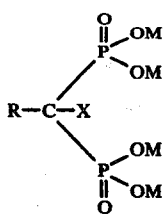

wherein X is H, OH or $NH_2$; M is hydrogen, a pharmaceutically-acceptable cation, e.g., alkali metal, especially Na or K or an alkyl or aryl moiety, e.g., methyl, ethyl, propyl, butyl, phenyl, or the like; and R is a $C_2$, or higher, hydrocarbyl group such as alkyl, cycloalkyl, or substituted $C_2$ or higher alkyl or cycloalkyl group. The term "hydrocarbyl" herein includes unsaturated and substituted alkyl, alkenyl and alkynyl and carbocyclic groups.

The phosphonate compounds employed herein are all known in the art and can be prepared by the general procedures described in ORGANIC PHOSPHORUS COMPOUNDS Vol. 7, Kosolapoff and Maier (1976) and references cited therein, as well as in the complete discussion of references to the preparation of such compounds disclosed in the U.S. Patents of Francis, cited hereinabove, the disclosures of which are incorporated herein by reference.

U.S. Pat. No. 3,400,149, Quimby, et al., issued Sept. 3, 1968, and the references cited therein, also disclose various reactions which can be used to provide phosphonate compounds of the type employed in the practice of this invention.

The gist of the present invention is the discovery that phosphonates of the above formula wherein R is at least a $C_2$ hydrocarbyl, e.g., alkyl, substituent desirably and unexpectedly affect glucose metabolism in a manner not seen with shorter-chain geminal diphosphonates such as ethane-1-hydroxy-1,1-diphosphonate, methane diphosphonate, dichloromethane diphosphonate, and the like.

Preferred phosphonate compounds herein are those wherein R is in the range of ca. $C_6$–$C_{13}$ alkyl, e.g., hexyl, octyl, decyl, undecyl and dodecyl; or cycloalkyl, especially cyclohexyl; or substituted alkyl, especially aminoalkyl; and wherein X is H or OH. As will be seen from the results of the cell culture experiments hereinafter, these kinds of compounds cause an increase in glucose consumption (and a concomitant increase in lactate production) to a level which is as much as three-fold greater than that of control cell cultures.

The following experiments demonstrate the heretofore unsuspected utility of certain phosphonate compounds for desirably affecting the metabolism of glucose. In the experiments, the term "MEM" means Minimum Essential Medium (Gibco); the meanings of all other terms and abbreviations are defined or are apparent from the text.

Methods

Cell Culture

Calvariae of one-day old Wistar rats were used. After decapitation the heads were kept for one hour in cold MEM with low $NaHCO_3$ (227 mg/l) containing 100 units penicillin, 100 mcg streptomycin, 0.25 mcg fungizone and 100 mcg mycostasin per ml, to kill bacteria and especially fungi found on rats. The calvariae were dissected and cleaned. 12–15 Calvariae were shaken for two hours at 37° C. in a 25 ml Erlenmeyer flask containing 4 ml MEM with 227 mg/l $NaHCO_3$, 100 units/ml penicillin, 100 mcg/ml streptomycin, 0.25 mcg/ml fungizone (=antibiotica) and 3 mg/ml collagenase (Worthington CLS II). The free cells were then harvested and plated in costar culture dishes 3524, 16 mm diameter (Tecnomara AG, Zurich, Switzerland) at a density of 40,000 cells per dish. Each dish contained 0.5 ml MEM with 10% fetal calf serum, 2.2 g/l $NaHCO_3$ and antibiotics and was incubated at 37° C. at 5% $CO_2$. The next day new medium with or without diphosphonates was added. This medium was then replaced every third day. On day 7 new medium was added and incubated for 16 hours in order to measure the lactate production and the glucose consumption. After the incubation the cells were released from the plate and counted.

Determination of cell number

After the media was removed, 0.25 ml of a mixture of 5 parts Hank's solution without $CaCl_2$, and 1 part MEM with 2.2 g/l $NaHCO_3$, containing 0.025% trypsin (Gibco) and 1 mg/ml collagenase (Worthington CLS II) was added to the monolayer and incubated for three hours at 37° C. at 5% $CO_2$. The cells were then suspended in 50 ml Hank's solution and counted on a Coulter Counter Model Industrial D, Coulter Counter Electronic Ltd., Dunstable, Beds, England.

Determination of glucose and lactate

Glucose was determined using hexokinase and glucose 6-phosphate dehydrogenase; for the lactate determination lactate dehydrogenase was used.

Expression of results

Dodecane-1-hydroxy-1,1-diphosphonate and nonanediphosphonate at 0.25 mM induced death of the cells. Therefore they were used at a concentration of 0.025 mM. $C_4H_3O_{10}P_2Na_5$ (A) and also to some degree ethane-1-amino-1,1-diphosphonate precipitated in the medium at 0.25 mM, but compound (A) did not precipitate at 0.025 mM. According to some observations it appeared that cells cultured in the presence of 0.25 mM of compound (A) and 0.025 of ethane-1-amino-1,1-diphosphonate were not so easily released from the dish by collagenase-trypsin digestion as other cells.

The cell number, the lactate production and the glucose consumption given as percentage of the control are shown in Tables I, II and III. The lowest cell number was found in the presence of diphosphonates with an aliphatic side group and also with $Cl_2MDP$. The lactate production and glucose consumption was most strongly reduced by diphosphonates which contained electrophilic groups. On the other hand, compounds with an aliphatic side group increased the lactate production and the glucose consumption.

In Tables I, II and III, the abbreviated terms have the following meanings: PPi is inorganic pyrophosphate; $Cl_2MDP$ is dichloromethane diphosphonate; ABDP is amino butane-1,1-diphosphonate; PAMDP is phenylamino-methane diphosphonate; EADP is ethane-1-amino-1,1-diphosphonate; McHDP is methane-1-hydroxy-1-cyclohexyl-1,1-diphosphonate; MDP is methanediphosphonate; and DMAMDP is dimethylamino-methane-diphosphonate.

The geminal diphosphonates herein are readily soluble in water or gastric juices and as can be seen from the data in Tables II and III, the longer-chain alkyl and cyclohexyl phosphonates substantially increase glucose metabolism over the short-chain alkyl compounds. The $C_9$, $C_{11}$ and $C_{12}$ alkyl compounds were especially effective in this regard, as was the cyclo-$C_6$ compound. Of the compounds tested, the shorter-chain compounds had little effect, unless substituted by an amino group (ABDP). However, the effect of these shorter-chain compounds is more comparable with inorganic pyrophosphate than with the superior undecane- and dodecane-1-hydroxy-1,1-diphosphonate and nonane-1,1-diphosphonate compounds tested. Accordingly, preferred for use in the practice of this invention are those 1,1-alkyldiphosphonates and 1-hydroxy-1,1-alkyldiphosphonates, wherein the alkyl group is longer than about $C_6$, preferably from about $C_8$ to about $C_{14}$.

Table I

Effect of Diphosphonates on Cell Number

| Compound | Concentration mM | Average Percentage of Control |
|---|---|---|
| $C_5H_2O_6P_2F_6Na_2$ | 0.25 | 116.2/94.2 |
| $C_4H_3O_{10}P_2Na_5$ | 0.25 | 73.4 |
| " | 0.025 | 87.7/80.6 |
| $CH_4O_7P_2Na_2$ | 0.25 | 94.4/61.9 |
| $C_5H_{14}O_6P_2$ | 0.25 | 86.0/69.8 |
| $C_{12}H_{28}O_7P_2$ | 0.025 | 56.4/49.0 |
| $C_9H_{20}O_6P_2Na_2$ | 0.025 | 57.6 |
| $CO_7P_2Na_4$ | 0.25 | 86.8/69.9 |
| $CH_4O_8P_2Na_2$ | 0.25 | 80.2/62.4 |
| $C_{11}H_{23}O_7P_2Na$ | 0.025 | 42.2 |
| PPi | 0.25 | 112.5/100.9 |
| " | 0.1 | 93.9 |
| $Cl_2MDP$ | 0.25 | 48.4 |
| " | 0.025 | 87.6 |
| ABDP | 0.25 | 78.1 |
| PAMDP | 0.25 | 101.9/88.7 |
| EADP | 0.25 | 49.0 |
| McHDP | 0.25 | 31.8 |
| MDP | 0.25 | 84.5 |
| DMAMDP | 0.25 | 107.1/89.5 |

Table II

Lactate Production per $10^6$ Cells

| Compound | Concentration mM | Average Percentage of Control |
|---|---|---|
| $C_5H_2O_6P_2F_6Na_2$ | 0.25 | 96.5/91.3 |
| $C_4H_3O_{10}P_2Na_5$ | 0.25 | 155.0 |
| " | 0.025 | 118/126 |
| $CH_4O_7P_2Na_2$ | 0.25 | 32.0/22.7 |
| $C_5H_{14}O_6P_2$ | 0.25 | 101.6/97.4 |
| $C_{12}H_{28}O_7P_2$ | 0.025 | 327.1/201.5 |
| $C_9H_{20}O_6P_2Na_2$ | 153.6 | |
| $CO_7P_2Na_4$ | 0.25 | 53.3/40.3 |
| $CH_4O_8P_2Na_2$ | 0.25 | 67.1/51.6 |
| $C_{11}H_{23}O_7P_2Na$ | 0.025 | 312 |
| PPi | 0.25 | 89.4/77.3 |
| " | 0.1 | 91.7 |
| $Cl_2MDP$ | 0.25 | 33.1 |
| " | 0.025 | 60.6 |
| ABDP | 0.25 | 152.3 |
| PAMDP | 0.25 | 88.5/108.3 |
| EADP | 0.25 | 160.9 |
| McHDP | 0.25 | 254.0 |
| MDP | 0.25 | 89.8 |
| DMAMDP | 0.25 | 88.2/106.6 |

Table III

Glucose Consumption per $10^6$ Cells

| Compound | Concentration mM | Average Percentage of Control |
|---|---|---|
| $C_5H_2O_6P_2F_6Na_2$ | 0.25 | 95.0/109.3 |
| $C_4H_3O_{10}P_2Na_5$ | 0.25 | 152.0 |

Table III-continued

Glucose Consumption per $10^6$ Cells

| Compound | Concentration mM | Average Percentage of Control |
|---|---|---|
| " | 0.025 | 136.3/86.4 |
| $CH_4O_7P_2Na_2$ | 0.25 | 18.0/49.6 |
| $C_5H_{14}O_6P_2$ | 0.25 | 88.5/110.3 |
| $C_{12}H_{28}O_7P_2$ | 0.025 | 306.2/197.6 |
| $C_9H_{20}O_6P_2Na_2$ | 0.025 | 153.5 |
| $CO_7P_2Na_4$ | 0.25 | 38.3/55.6 |
| $CH_4O_8P_2Na_2$ | 0.25 | 50.9/63.8 |
| $C_{11}H_{23}O_7P_2Na$ | 0.025 | 279 |
| PPi | 0.25 | 91.2/90.7 |
| " | 0.1 | 116.5 |
| $Cl_2MDP$ | 0.25 | 43.9 |
| " | 0.025 | 70.4 |
| ABDP | 0.25 | 142.9 |
| PAMDP | 0.25 | 96.0/70.1 |
| EADP | 0.25 | 118.9 |
| McHDP | 0.25 | 172.6 |
| MDP | 0.25 | 91.9 |
| DMAMDP | 0.25 | 94.1/112.5 |

PREFERRED MODE

Within the scope of sound medical judgment, the dosage of the phosphonates herein will vary with the particular condition being treated, the severity of the condition, the duration of treatment, and like factors within the specific knowledge and expertise of the attending physician. However, single dosages can typically range from 0.01 to 500 mg per kilogram of body weight, preferably 0.5 to 50 mg/kg (unless otherwise specified, the unit designated "mg/kg" as used hereinm refers to mg/kg of body weight). The higher dosages within this range are usually required in the case of oral administration because of somewhat limited absorption of the phosphonates through the gut. Up to four dosages per day can be used routinely, but this can be varied to the needs of the patient, consistent with a sound benefit:risk ratio. Dosages greater than about 500 mg/kg may produce untoward symptoms and are usually avoided; moreover, daily dosages greater than about 2,000 mg/kg are not ordinarily required to produce the desired benefit and may produce toxic side effects. Again, however, patient-to-patient variations in response may be expected. Dosages of about 0.01 mg/kg are useful, especially if administered intravenously.

Preferably, dosages ranging from about 10 to about 100 mg/kg are employed when the phosphonates are administered orally, since absorption is not total.

For parenteral administration (s.c., i.p., i.m.), phosphonate dosages are preferably from about 0.5 mg/kg/day to about 20 mg/kg/day. For long-term parenteral infusion (i.v.) the most highly preferred dosage range is from about 0.5 mg/kg/day to about 5 mg/kg/day.

For purposes of oral administration the phosphonates herein can be formulated in the form of capsules, tablets or granules. For treatment of non-human animals, the phosphonates are preferably incorporated in animal feed, feed supplements or feed concentrates. They can also be prepared in unit dosage form together with a pharmaceutical carrier, each unit dosage form containing from ca. 15 mg to 10 g of phosphonate. The preferred concentration range of phosphonate in unit dosage forms intended for use by humans and smaller domesticated animals is from 15 mg to 1,000 mg, more preferably 100 mg to 500 mg. A higher concentration range, i.e., from 1 g to 5 g is preferred in unit dosage forms intended for treatment of larger animals such as cattle, horses, etc.

As used herein, the term "pharmaceutical carrier" denotes a solid or liquid filler diluent or encapsulating substance. Some examples of the substances which can serve as pharmaceutical carriers are sugars such as lactose, glucose and sucrose; starches such as corn starch and potato starch; cellulose and its derivatives, such as sodium carboxymethylcellulose, ethylcellulose, cellulose acetate; powdered tragacanth; malt; gelatin; talc; stearic acid; magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; agar; alginic acid; pyrogen-free water; isotonic saline; and phosphate buffer solutions, as well as other non-toxic compatible substances used in pharmaceutical formulations. Wetting agents and lubricants such as sodium lauryl sulfate, as well as coloring agents, flavoring agents and preservatives can also be present. Tableting is done using conventional techniques.

The pharmaceutical carrier employed in conjunction with the phosphonates is used at a concentration sufficient to provide a practical size to dosage relationship. Preferably, the pharmaceutical carrier comprises from about 0.1% to 99% by weight of the total composition.

Animal feed compositions to which the phosphonates of this invention can be added generally include as feedstuffs a cellulosic roughage component such as hay, straw, plant hulls, corn cobs, etc. Protein-containing components such as whole grains, including corn, wheat, barley, oats, rye, millet and alfalfa are typically included.

The following examples illustrate compositions and methods used in the practice of this invention, but are not intended to be limiting thereof.

EXAMPLE I

Gelatin capsules are prepared by conventional methods, comprising as follows:

| Ingredient | Mg per capsule |
| --- | --- |
| DHDP* | 350.0 |
| Starch | 50.0 |

*Dodecane-1-hydroxy-1,1-diphosphonate, mixture of di- and tri-sodium salts.

The above capsules are administered twice daily to substantially increase glucose metabolism in diabetic patients having need of such treatment.

Similar results to those obtained with the capsules of Example I are secured when the DHDP, Na salt, is replaced by an equivalent amount of DHDP (free acid form), and the following phosphonates, respectively: ABDP (Na salt); EADP (Na and K salts); McHDP (Na, K salts and ethyl esters); nonane-1,1-diphosphonate (disodium salt); and undecane-1-hydroxy-1,1-diphosphonate (monosodium salt).

EXAMPLE II

Tablets are prepared by conventional methods, formulated as follows:

| Ingredient | Mg per Tablet |
| --- | --- |
| McHDP* | 250.00 |

-continued

| Ingredient | Mg per Tablet |
| --- | --- |
| Lactose | 40.00 |
| Starch | 2.50 |
| Magnesium stearate | 1.00 |

*Mixture of di- and tri-sodium salts.

The above composition is administered orally four times daily to increase glucose metabolism in a patient weighing approximately 70 kilograms, having a predisposition to carbohydrate intolerance.

Similar results are achieved with tablets formulated as above but replacing McHDP with $C_{12}H_{28}O_7P_2$, $C_9H_{20}O_6P_2Na_2$, $C_{11}H_{23}O_7P_2Na$, ABDP and EADP, respectively.

EXAMPLES III–VIII

The phosphonates can also be administered parenterally in aqueous solution by subcutaneous, intradermal, intramuscular or intravenous injection, or i.v. infusion. The usual, and preferred, dosage ranges by these modes of administration are as follows:

| | |
| --- | --- |
| Subcutaneous | 0.05–10 mg/kg |
| Intradermal | 0.05–10 mg/kg |
| Intramuscular | 0.05–5 mg/kg |
| Intravenous | 0.05–5 mg/kg |

Solutions for parenteral administration are prepared by dissolving the indicated phosphonic acids in distilled water at the specified concentration, adjusting the pH to 7.4 with the base corresponding to the indicated salt form, and sterilizing same by standard sterilization techniques.

| Ex. | Phosphonate | Conc. mg/ml |
| --- | --- | --- |
| III | McHDP, K | 10.0 |
| IV | McHDP, $K_2$ | 15.0 |
| V | DHDP, $Na_2$ + $Na_3$ mixture | 5.0 |
| VI | $C_{11}H_{23}O_7P_2$, Na | 5.0 |
| VII | McDP, Na | 13.0 |
| VIII | DHDP, $NH_4^+$ | 18.0 |

The solutions of the foregoing examples are administered by injection to animals (including humans) in an amount sufficient to provide desired dosage levels as hereinbefore specified to enhance carbohydrate metabolism. Preferably, the solutions are packaged in sealed ampules for single dosage hypodermic injections.

EXAMPLE IX

A complete feed composition embodying the present invention and useful for enhancing carbohydrate metabolism in animals is as follows:

| Component | Parts by Weight |
| --- | --- |
| Timothy hay | 960 |
| Dehydrated alfalfa | 40 |
| Yellow corn | 600 |
| Iodized salt | 10 |
| Bone meal | 20 |
| McHDP (acid form) | 40 |

As can be seen from the foregoing, the present invention provides a means for desirably affecting the metabolism of carbohydrates, especially glucose, and thereby provides a means for treating diabetes and diabetes-like disease states. The processes herein are preferably carried out using geminal diphosphonate compounds selected from the group consisting of the pharmaceutically-acceptable $C_8$–$C_{14}$ alkyl- and cyclohexylmethyl-1-hydroxy-1,1-diphosphonates and the $C_8$–$C_{14}$ alkyl- and cyclohexylmethyl-1,1-diphosphonates. In particular, the processes of this invention are preferably carried out with the geminal diphosphonates octyl-, nonyl-, decyl-, undecyl- (preferred), dodecyl- (preferred), tridecyl- and tetradecyl-1-hydroxy-1,1-disphosphonates, and the pharmaceutically-acceptable salts and esters thereof; with octyl-, nonyl- (preferred), decyl-, undecyl-, dodecyl-, tridecyl- and tetradecyl-1,1-diphosphonates, and the pharmaceutically-acceptable salts and esters thereof; and with methane-1-hydroxy-1-cyclohexyl-1,1-diphosphonate (preferred), methanecyclohexyl-1,1-diphosphonate, and the pharmaceutically-acceptable salts and esters thereof.

What is claimed is:

1. A process for treating *diabetes mellitus* in humans and lower animals, comprising administering to a human or lower animal in need of such treatment a safe and effective amount of ethane-1-amino-1,1-diphosphonic acid, or a pharmaceutically-acceptable salt thereof.

* * * * *